United States Patent
Cheng et al.

(10) Patent No.: US 6,516,209 B2
(45) Date of Patent: Feb. 4, 2003

(54) SELF-CALIBRATING OPTICAL IMAGING SYSTEM

(75) Inventors: Xuefeng Cheng, Milpitas, CA (US); Xiaorong Xu, Menlo Park, CA (US); Shuoming Zhou, Cupertino, CA (US); Lai Wang, Cupertino, CA (US); Ming Wang, San Jose, CA (US); Feng Li, San Jose, CA (US); Guobao Hu, San Jose, CA (US)

(73) Assignee: Photonify Technologies, Inc., Fremont, CA (US)

(*) Notice: Subject to any disclaimer, the term of this patent is extended or adjusted under 35 U.S.C. 154(b) by 0 days.

(21) Appl. No.: 09/778,618

(22) Filed: Feb. 6, 2001

(65) Prior Publication Data

US 2002/0019587 A1 Feb. 14, 2002

Related U.S. Application Data

(60) Provisional application No. 60/223,074, filed on Aug. 4, 2000.

(51) Int. Cl.[7] .................................................. A61B 5/00
(52) U.S. Cl. ........................ 600/323; 600/310; 600/473; 600/476; 250/252.1
(58) Field of Search .................................. 600/310, 322, 600/323, 328, 473, 475, 476; 250/252.1, 341.1

(56) References Cited

U.S. PATENT DOCUMENTS

| | | |
|---|---|---|
| 3,963,351 A | 6/1976 | Chance et al. |
| 4,555,179 A | 11/1985 | Langerholc et al. |
| 4,810,875 A | 3/1989 | Wyatt |
| 4,829,184 A | 5/1989 | Nelson et al. |
| 5,119,815 A | 6/1992 | Chance |
| 5,137,355 A | 8/1992 | Barbour et al. |
| 5,167,230 A | 12/1992 | Chance |
| 5,402,778 A | 4/1995 | Chance |
| 5,555,885 A | 9/1996 | Chance |
| 5,564,417 A | 10/1996 | Chance |
| 5,596,987 A | 1/1997 | Chance |
| 5,664,574 A | 9/1997 | Chance |
| 5,676,143 A | 10/1997 | Simonsen et al. |
| 5,782,755 A | 7/1998 | Chance et al. |

(List continued on next page.)

OTHER PUBLICATIONS

Hueber et al., *"New Optical Probe Designs For Absolute (Self–Calibrating) NIR Tissue Hemoglobin Measurements"* SPIE Conference on Optical Tomography and Spectroscopy of Tissue III, SPIE vol. 3597, Jan. 1999, pp. 618–631.

(List continued on next page.)

*Primary Examiner*—Eric F. Winakur
(74) *Attorney, Agent, or Firm*—Pennie & Edmonds LLP

(57) ABSTRACT

The present invention generally relates to optical imaging systems and methods for providing images of two-dimensional and/or three-dimensional distribution of properties of chromophores in various physiological media. More particularly, the present invention relates to optical imaging systems, optical probes thereof, and methods therefore utilizing self-calibration of their output signals. A typical self-calibrating optical imaging system includes at least one wave source, at least one wave detector, a signal analyzer, a signal processor, and an image processor. The signal analyzer receives, from the wave detector, an output signal representative of the distribution of the chromophores or their properties in target areas of the medium. The signal analyzer analyzes amplitudes of the output signal and selects multiple points of the output signal having substantially similar amplitudes. The signal processor calculates a baseline corresponding to a representative amplitude of the similar amplitudes and provides a self-calibrated output signal. The image processor constructs the images of the distribution of the chromophores or their properties from the self-calibrated first output signals.

50 Claims, 7 Drawing Sheets

U.S. PATENT DOCUMENTS

| | | | |
|---|---|---|---|
| 5,792,051 A | 8/1998 | Chance | |
| 5,803,909 A | 9/1998 | Maki et al. | 600/310 |
| 5,807,263 A | 9/1998 | Chance | |
| 5,820,558 A | 10/1998 | Chance | |
| 5,835,617 A | 11/1998 | Ohta et al. | |
| 5,853,370 A | 12/1998 | Chance et al. | |
| 5,865,754 A | 2/1999 | Sevick-Muraca et al. | |
| 5,873,821 A | 2/1999 | Chance et al. | |
| 5,899,865 A | 5/1999 | Chance | |
| 5,917,190 A | 6/1999 | Yodh et al. | |
| 5,954,053 A | 9/1999 | Chance et al. | |
| 5,987,346 A | 11/1999 | Benaron et al. | 600/407 |
| 5,987,351 A | 11/1999 | Chance | |
| 6,058,324 A | 5/2000 | Chance | |
| 6,078,833 A * | 6/2000 | Hueber | 600/310 |
| 6,088,605 A | 7/2000 | Griffith et al. | 600/316 |
| 6,104,945 A * | 8/2000 | Modell et al. | 600/473 |
| 6,134,460 A | 10/2000 | Chance | |
| 6,151,518 A | 11/2000 | Hayashi | 600/322 |
| 6,192,260 B1 | 2/2001 | Chance | |
| 6,272,367 B1 | 8/2001 | Chance | |
| 6,304,771 B1 | 10/2001 | Yodh et al. | |

OTHER PUBLICATIONS

Chance et al., 1998, "A novel method for fast imaging of brain function, non–invasively, with light," *Optics Express* 2(10):411–423.

Cubeddu et al., 1998, "In vivo absorption and scattering spectra of human tissues in the red and near infrared," *TOPS 21*: 271–274.

Du et al., 1998, "Quantitative detection of hemoglobin saturation on piglet brain by near–infrared frequency–domain spectroscopy," *Proceedings of Photon Propagation in Tissues III (SPIE) 3194*:55–62.

Fantini et al., 1999, "Non–invasive optical mapping of the piglet brain in real time," *Optics Express* 4(8):308–314.

Ma et al., "Quantitative study of hypoxia stress in piglet brain by IQ phase modulation oximetry," *Part of the SPIE Conference on Optical Tomography and Spectroscopy of Tissue III*, San Jose, California. Jan. 1999. SPIE vol. 3597, pp. 642–649.

Pogue et al., 1997, "Instrumentation and design of a frequency–domain diffuse optical tomography imager for breast cancer detection," *Optics Express* 1(13):391–403.

Siegel et al., "Diffuse optical tomography of rat brain function," *Part of the SPIE Conference on Optical Tomography and Spectroscopy of Tissue III*, San Jose, California. Jan. 1999. SPIE vol. 3597, pp. 252–261.

* cited by examiner

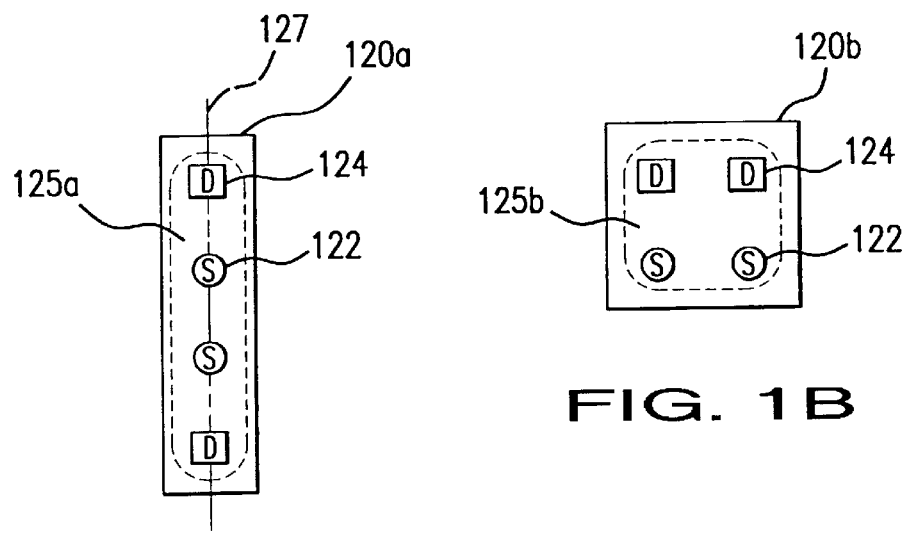
FIG. 1A
FIG. 1B
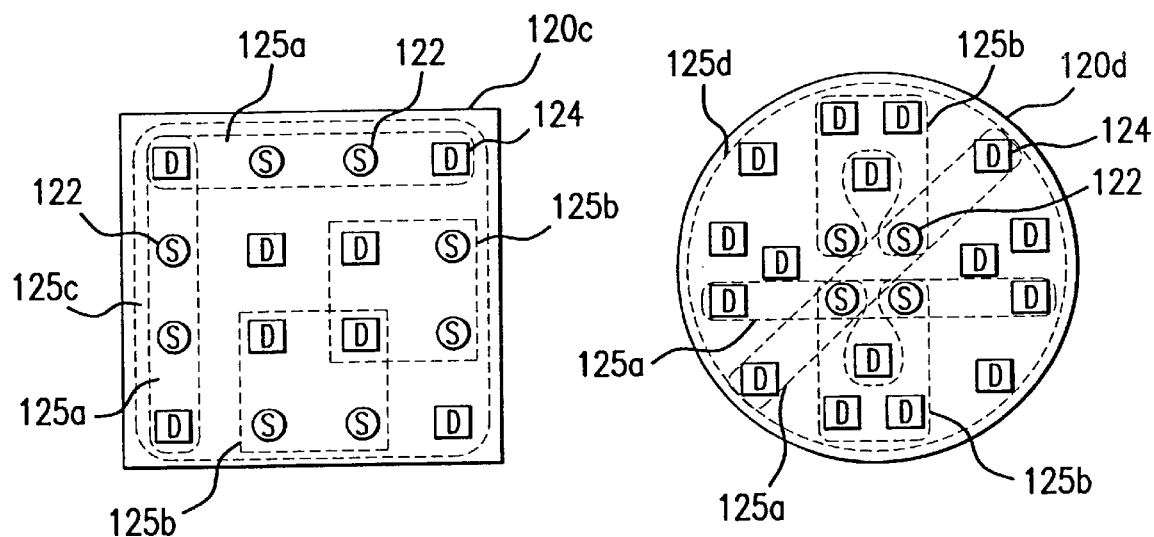
FIG. 1C
FIG. 1D

SELF-CALIBRATING OPTICAL IMAGING SYSTEM

CROSS-REFERENCE TO RELATED APPLICATIONS

This application claims the benefit of the filing date of U.S. Provisional Patent Application bearing Serial No. 60/223,074, entitled "A Self-Calibrated Optical Scanner for Diffuse Optical Imaging" and filed on Aug. 4, 2000.

FIELD OF THE INVENTION

The present invention generally relates to optical imaging systems, optical probes thereof, and methods thereof for providing images of spatial or temporal distribution of chromophores or properties thereof in a physiological medium. In particular, the present invention relates to a self-calibrating optical imaging system. The present invention is applicable to optical imaging systems whose operation is based on wave equations such as the Beer-Lambert equation, modified Beer-Lambert equation, photon diffusion equation, and their equivalents.

BACKGROUND OF THE INVENTION

Near-infrared spectroscopy has been used to measure various physiological properties in animal and human subjects. The basic principle underlying the near-infrared spectroscopy is that a physiological medium such as tissues and cells includes a variety of light-absorbing and light-scattering chromophores which can interact with electromagnetic waves transmitted thereto and traveling therethrough. For example, human tissues include numerous chromophores among which deoxygenated and oxygenated hemoglobins are the most dominant chromophores in the spectrum range of 600 nm to 900 nm. Therefore, the near-infrared spectroscope has been applied to measure oxygen levels in the physiological medium in terms of tissue hemoglobin oxygen saturation (or simply "oxygen saturation" hereinafter). Technical background for the near-infrared spectroscopy and diffuse optical imaging has been discussed in, e.g., Neuman, M. R., "Pulse Oximetry: Physical Principles, Technical Realization and Present Limitations," *Adv. Exp. Med. Biol.*, vol. 220, p.135–144, 1987, and Severinghaus, J. W., "History and Recent Developments in Pulse Oximetry," *Scan. J. Clin. and Lab. Investigations*, vol. 53, p.105–111, 1993.

Various techniques have been developed for the near-infrared spectroscopy, including time-resolved spectroscopy (TRS), phase modulation spectroscopy (PMS), and continuous wave spectroscopy (CWS). In a homogeneous, semi-infinite model, the TRS and PMS are generally used to solve the photon diffusion equation, to obtain the spectra of absorption coefficients and reduced scattering coefficients of the physiological medium, and to estimate concentrations of the oxygenated and deoxygenated hemoglobins and oxygen saturation. The CWS has generally been used to solve the modified Beer-Lambert equation and to calculate changes in the concentrations of the oxygenated as well as deoxygenated hemoglobin.

Despite their capability of providing hemoglobin concentrations as well as the oxygen saturation, the major disadvantage of the TRS and PMS is that the equipment has to be bulky and, therefore, expensive. The CWS may be manufactured at a lower cost but is generally limited in its utility, for it can estimate only the changes in the hemoglobin concentrations but not the absolute values thereof Accordingly, the CWS cannot provide the oxygen saturation. The prior art technology also requires a priori calibration of optical probes before their clinical application by, e.g., measuring a baseline in a reference medium or in a homogeneous portion of the medium. Furthermore, all prior art technology employs complicated image reconstruction algorithms to generate images of two-dimensional and/or three-dimensional distribution of the chromophore properties.

Therefore, there exist needs for an efficient, compact, and relatively cheap optical imaging system which self-calibrates itself without relying on external measurement or data and which provides two- and/or three-dimensional images on a substantially real time basis.

SUMMARY OF THE INVENTION

The present invention generally relates to optical imaging systems, optical probes, signal and/or image processing algorithms, and methods thereof for providing two- or three-dimensional images of spatial or temporal distribution of chromophores or their properties in a physiological medium. More particularly, the present invention relates to novel self-calibrating optical imaging systems and methods thereof.

In one aspect of the present invention, an optical imaging system is provided to generate images of distribution of chromophores or their properties in target areas of various physiological media. The optical imaging system includes at least one wave source arranged to irradiate electromagnetic waves into the target areas of the medium and at least one wave detector arranged to detect electromagnetic waves from the target areas and to generate output signal in response thereto. The optical imaging system further includes an optical probe, a signal analyzer, and a signal processor. The optical probe typically includes the wave source and wave detector. The signal analyzer receives, from the wave detector, a first output signal which is representative of the distribution of the chromophores or their properties in a first target area of the medium. The signal analyzer analyzes an amplitude of each point of the first output signal and selects one or more points or portions of the first output signal having substantially similar first amplitudes. The signal processor calculates a first baseline from the first output signal, where the first baseline generally corresponds to a representative amplitude of the first amplitudes of the foregoing points or portions, and provides a self-calibrated first output signal by manipulating the first output signal and first baseline thereof. Therefore, the optical imaging system provides the self-calibrated output signal representing a spatial distribution and/or temporal variation of the chromophores or their properties in the first target area.

The foregoing optical imaging systems, probes, algorithms, and methods (collectively referred to as "optical imaging system" or "optical probe" hereinafter) of the present invention provide numerous advantages. Contrary to the prior art optical imaging devices that require a priori measurement and estimation of an output signal baseline in a reference medium (or area) before their clinical applications, the optical imaging system of the present invention allows a user to directly scan a target area, to obtain the output signal, and to simultaneously obtain the baseline of the output signal. Accordingly, the optical imaging system of the present invention obviates the need for a prior estimation of the baseline in other reference media (or areas). In addition, because the foregoing optical imaging system can estimate the baseline and the output signals from the same target area, it does not suffer from noises or errors attributed to different optical characteristics between the reference and target areas. Furthermore, due to simpler algorithms for estimating the baseline, the optical imaging system of the present invention allows real-time calibration of the output signals and, therefore, contributes to the real-time construction of images of the distribution of the chromophore or its properties.

Embodiments of this aspect of the present invention includes one or more of the following features.

The optical probe includes a scanning area which is almost equal to or as large as at least a substantial portion of the first target area of the medium. Multiple wave sources and detectors are disposed in the scanning area so that the chromophore properties in the first target area can be measured by a single measurement in the first target area. In the alternative, the optical probe may include a scanning area which may be only a small region of the first target area. In this embodiment, the optical imaging system includes an actuator member arranged to move at least one of the wave source and wave detector so that at least a substantial portion of the first target area can be scanned thereby. Accordingly, the wave detector can generate multiple first output signals while the optical probe or its main housing is positioned and maintained stationary in the first target area. This embodiment allows construction of compact optical probes with a minimal number of the wave sources and/or detectors implemented thereto. In addition, such optical probes can minimize the noises or errors attributed to idiosyncratic component variations among system components.

The foregoing optical imaging system may also include an image processor which constructs the images of the distribution of the chromophores or properties thereof from the self-calibrated first output signals, preferably on a substantially real-time basis. The signal analyzer and processor may also operate on a substantially real-time basis and provide the self-calibrated first output signal without displacing the optical probe from the first target area. The optical imaging system may further include a memory for storing the first output signal, first baseline, self-calibrated first output signal, and other signals or data.

The signal analyzer may include a threshold unit for obtaining a threshold amplitude, a comparison unit for comparing the amplitudes of the points or portions of the first output signal with the threshold amplitude, and a selection unit for identifying multiple selected points or portions of the first output signal. The threshold unit may receive the threshold amplitude from a user. Alternatively, the threshold unit may calculate a reference amplitude based on the first output signal and then calculate the threshold amplitude from the reference amplitude, where the reference amplitude may be, e.g., a local maximum or minimum of the first output signal measured in the first target area, an average of at least one or entire portion of the first output signal, a global maximum or minimum of multiple output signals measured in multiple target areas over the medium, and their combinations. The threshold amplitude may be calculated as a product of the reference amplitude and a pre-determined factor which may be encoded therein or may be provided by the operator. Therefore, depending on the mode of selecting the threshold amplitude, the first amplitudes of the selected points or portions may be either greater or less than the threshold amplitude.

Alternatively, the signal analyzer may include a threshold unit for obtaining a threshold range of amplitudes, a comparison unit for comparing the amplitudes of the points or portions of the first output signal with the threshold range, and a selection unit arranged to identify those selected points or portions of the first output signal. Accordingly, the first amplitudes of the selected points may fall within or outside the threshold range.

The signal analyzer may also include a filter unit arranged to improve signal-to-noise ratio of the first output signals. The filter unit may include an algorithm arranged to arithmetically, geometrically, weight- or ensemble-averaging multiple first output signals. The filter unit may also include a low pass filter for removing high frequency noises from the first output signal.

The signal processor may include an averaging unit for calculating the first baseline by arithmetically, geometrically, weight- or ensemble-averaging the substantially similar first amplitudes of the foregoing points or portions. The signal processor may also include a calibration unit for obtaining the self-calibrated first output signal by normalizing the first output signal by its first baseline, where the self-calibrated first output signal may be defined as a ratio of the first output signal to the first baseline or a ratio of a difference between the first output signal and first baseline to the first baseline.

The signal analyzer may also include a control unit which stores multiple baselines measured in multiple target areas and compares one or each baseline from the others thereof. The control unit may calculate an average of such multiple baselines. The control unit may be arranged send a signal or alarm to the operator when at least one of the baselines is at least substantially different from at least one of the others.

In another aspect of the invention, an optical imaging system is provided to generate images of distribution of chromophores or their properties in target areas of a physiological medium. The optical imaging system includes at least one of the foregoing wave sources and at least one of the foregoing wave detectors. The optical imaging system also includes a signal analyzer, signal processor, and image processor. The signal analyzer receives, from the wave detector, a first output signal representative of the foregoing distribution in a first target area of the medium, analyzes amplitudes of the first output signal, and selects multiple points or portions of the first output signal having substantially similar first amplitudes. The signal processor calculates, from the first output signal, a first baseline which corresponds to a representative value of the first amplitudes, and provides a self-calibrated first output signal by manipulating both of the first output signal and its first baseline. The image processor constructs the images of the foregoing distribution from the self-calibrated first output signals.

In yet another aspect of the present invention, an optical imaging system is provided to generate images of the foregoing distribution in target areas of a physiological medium. The optical imaging system includes at least one of the foregoing wave sources and at least one of the foregoing wave detectors along with a movable member, actuator member, signal analyzer, signal processor, and image processor. The movable member includes at least one of the wave source and detector, and the actuator member generates at least one movement of the movable member. The signal analyzer receives, from the wave detector, a first output signal representing the foregoing distribution in a first target area of the medium, analyzes an amplitude of each point of the first output signal, and selects multiple points or portions of the first output signal having substantially similar first amplitudes. The signal processor calculates, from the first output signal, a first baseline which corresponds to a representative amplitude of the first amplitudes, and provides a self-calibrated first output signal by manipulating the first output signal and its first baseline. The image processor then constructs the images of the foregoing distribution from the self-calibrated first output signals.

In a further aspect of the present invention, a method is provided to obtain a calibrated output signal from an optical imaging system which includes an optical probe with the foregoing wave source and detector. The method includes the steps of positioning the optical probe on a first target area of said medium, generating a first output signal without displacing the optical probe from the first target area, identifying at least one first portion of the first output signal having substantially similar first amplitudes, and obtaining a first baseline of the first output signal from a representative value of the foregoing first portion having the first amplitudes.

Embodiments of this aspect of the present invention includes one or more of the following features.

The method may also include the step of normalizing the first output signal by the first baseline to provide a self-calibrated first output signal. In addition, the method may include the step of reducing noise from the first output signal prior to performing the foregoing identifying and obtaining steps. The reducing step may include the step of, e.g., arithmetically, geometrically, weight- or ensemble-averaging multiple first output signals or the step of processing at least a portion of the first output signal through a low-pass filter.

The generating step may include the step of providing movement of at least one of the wave source and detector over the different regions of the first target area, while generating the first output signal during such movement.

The identifying step may include the step of selecting a threshold amplitude and identifying the first portion of the first output signal having the amplitudes greater or less than the threshold amplitude. The identifying step may alternatively include the steps of selecting at least one threshold range and identifying the first portion which has the amplitudes within or outside the threshold range. Such selecting steps may be manually selecting the threshold amplitude and/or range, or identifying a reference amplitude or range and providing the threshold amplitude and/or range therefrom. The reference amplitude may be selected as a local maximum or minimum of the first output signal measured in the first target area, an average of one or entire portion of the first output signal, a global maximum or minimum of multiple output signals measured in multiple target areas over the medium, and a combination thereof.

The obtaining step may include one of arithmetically, geometrically, and/or weight-averaging the first amplitudes of the first portion of the first output signal.

The method may further include the steps of moving the optical probe to a second target area of the medium, generating a second output signal from the second target area, and normalizing the second output signal by the first baseline from the first target area to provide a self-calibrated second output signal. Such moving and generating steps may also be repeated in other target areas of the medium. Alternatively, the method may include the steps of moving the optical probe to a second target area of the medium, generating a second output signal from the second target area, identifying, from the second output signal, at least one second portion having substantially similar second amplitudes, and obtaining a second baseline of the second output signal corresponding to a representative amplitude of the second amplitudes. A composite baseline may be obtained by averaging the first and second baselines by arithmetically, geometrically, weight-, and/or ensemble-averaging such baselines or by manually selecting one of the baselines as the composite baseline.

In yet another aspect of the invention, yet another method is provided to obtain a calibrated output signal from an optical imaging system including the foregoing optical probe with the foregoing wave source and detector. The method includes the steps of positioning the optical probe on a first target area of a physiological medium with a normal region and an abnormal region, generating a first output signal without displacing the optical probe from the first target area, identifying from the first output signal at least one first portion of the first output signal attributed to the normal region of the target area, and obtaining a first baseline of the first output signal from a representative value of the first portion of the first output signal.

Embodiments of this aspect of the present invention includes one or more of the following features.

The method may also include the step of normalizing the first output signal by the first baseline to provide a self-calibrated first output signal. The first portion of the first output signal may have a substantially flat profile and/or such first portion may have substantially similar first amplitudes.

In a further aspect of the present invention, yet another method is provided for calibrating an optical imaging system which includes the foregoing optical probe with the foregoing wave source and detector. Such method includes the steps of positioning the optical probe on a first target area of a physiological medium, generating a first output signal without displacing the optical probe from the first target area, identifying from the first output signal at least one first portion which has substantially similar first amplitudes before displacing the optical probe from the first target area, and obtaining a first baseline of the first output signal which is a representative value of the similar first amplitudes before displacing the optical probe from the first target area.

Embodiments of this aspect of the present invention includes one or more of the following features.

The method may include the step of normalizing the first output signal by the first baseline to provide a self-calibrated first output signal on a substantially real time basis. The method may also include the step of generating images of the first output signal, images of the self-calibrated first output signal, images derived from the first output signal, and images derived from the self-calibrated first output signal.

Each of the foregoing optical imaging systems and methods of the present invention may incorporate analytical and/or numerical solution schemes disclosed in the commonly assigned co-pending U.S. non-provisional patent application bearing Ser. No. 09/664,972, entitled "A system and Method for Absolute Oxygen Saturation" by Xuefeng Cheng, Xiaorong Xu, Shuoming Zhou, and Ming Wang on Sep. 18, 2000 which is incorporated herein by reference in its entirety (referred to as "the '972 application" hereinafter). Therefore, the absolute values of concentration of oxygenated hemoglobin, [HbO], concentration of deoxygenated hemoglobin, [Hb], oxygen saturation, [$SO_2$], and temporal changes in blood volume may be obtained by any of the solution schemes of the co-pending '972 application, and images thereof may be provided to allow physicians to make direct diagnosis of the target area of the medium based on the "absolute" and/or "relative" values of the chromophore properties in the physiological media. In addition, operational characteristics of the optical imaging systems of the present invention are generally not affected by the precise number of the wave sources and/or detectors and by geometric arrangement therebetween.

As used herein, a "chromophore" means any substance in a physiological medium which can interact with electromagnetic waves transmitting therethrough. Such chromophore may include solvents of a medium, solutes dissolved in the medium, and/or other substances included in the medium. Specific examples of such chromophores may include, but not limited to, cytochromes, enzymes, hormones, proteins, cholesterols, lipids, apoproteins, chemotransmitters, neurotransmitters, carbohydrates, cytosomes, blood cells, cytosols, water, oxygenated hemoglobin, deoxygenated hemoglobin, and other materials present in the animal or human cells, tissues or body fluid. The "chromophore" may also include any extra-cellular substance which may be injected into the medium for therapeutic or imaging purposes and which may interact with electromagnetic waves. Typical examples of such chromophores may include, but not limited to, dyes, contrast agents, and/or other image-enhancing agents, each of which exhibits optical interaction with electromagnetic waves having wavelengths in a specific range.

"Hemoglobins" are oxygenated hemoglobin (i.e., HbO) and/or deoxygenated hemoglobin (i.e., Hb). Unless otherwise specified, "hemoglobins" refer to both oxygenated and deoxygenated hemoglobins. "Total hemoglobin" means the sum of the oxygenated and deoxygenated hemoglobins.

"Electromagnetic waves" as used herein may include acoustic or sound waves, near-infrared rays, infrared rays, visible light rays, ultraviolet rays, lasers, and/or photons.

"Property" of the chromophore refers to intensive property thereof such as concentration of the chromophore, a sum of concentrations thereof, a ratio thereof, and the like. "Property" may also refer to extensive property such as, e.g., volume, mass, weight, volumetric flow rate, and mass flow rate of the chromophore.

The term "value" is an absolute or relative value which represents spatial or temporal changes in the property of the chromophores (or hemoglobins).

"Distribution" refers to two-dimensional or three-dimensional distribution of the chromophores or their properties. The "distribution" may be measured or estimated in a spatial and/or temporal domain.

Unless otherwise defined, all technical and scientific terms used herein have the same meaning as commonly understood and/or used by one of ordinary skill in the art to which this invention belongs. Although methods and materials similar or equivalent to those described herein can be applied and/or used in the practice of or testing the present invention, suitable methods and materials are described below. All publications, patent applications, patents, and other references mentioned herein are incorporated by reference in their entirety. In case of conflict, the present application, including definitions, will control. In addition, the materials, methods, and examples are illustrative only and not intended to be limiting.

Other features and advantages of the invention will be apparent from the following detailed description and from the appended claims.

BRIEF DESCRIPTION OF THE DRAWINGS

FIGS. 1A to 1D are exemplary arrangements of wave sources and detectors of an optical imaging system according to the present invention;

DETAILED DESCRIPTION OF THE INVENTION

Figure 2A:
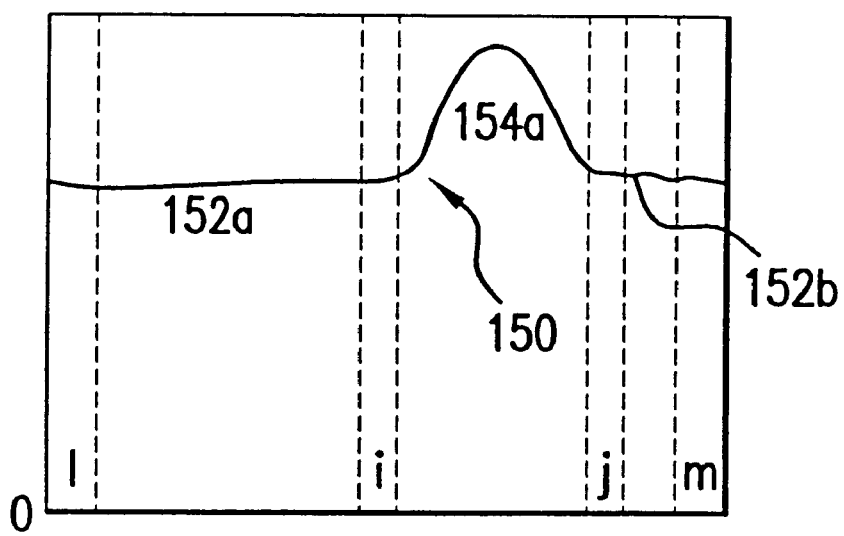
FIGS. 2A and 2B are exemplary output signals generated by wave detectors according to the present invention.

The following description provides various optical imaging systems arranged to provide images of two- and/or three-dimensional spatial and/or temporal distribution of properties of chromophores in a physiological medium. More particularly, the following description provides preferred aspects and embodiments of optical imaging systems, optical probes thereof, and methods thereof for calibrating their output signals.

FIGS. 1A through 1D are exemplary arrangements of wave sources and wave detectors of an optical imaging system according to the present invention. The exemplary optical imaging system typically includes an optical probe having a scanning surface 120a–120d on which multiple wave sources 122 and detectors 124 (both collectively referred to as "sensors" hereinafter) are disposed.

In general, each pair of wave source 122 and detector 124 forms a scanning element representing a functional unit from which wave source 122 emits electromagnetic waves into a target area of a medium and wave detector 124 detects electromagnetic waves interacted with and emanating from the target area of the medium. Wave detector 124 generates a corresponding output value signal or data point signal representing an amount of the electromagnetic waves detected thereby across the scanning element. A group of wave sources 122 and detectors 124 or a group of scanning elements also defines a scanning unit 125 which generally forms an effective scanning area of the optical probe of the invention. As a result, the group of sensors 122, 124 generates an output signal corresponding to a collection of multiple output value signals or data point signals each of which is generated in its corresponding scanning element. Configuration of scanning unit 125 and its scanning area is predominantly determined by geometric arrangements of a sensor assembly and/or source-detector arrangement such as, e.g., the number of wave sources 122 and detectors 124, geometric arrangement therebetween, grouping of wave sources 122 and detectors 124 for the scanning elements and for the scanning units, irradiation capacity or emission power of wave source 122, detection sensitivity of wave detector 124, and the like. For example, in the embodiment of FIG. 1A, two wave detectors 124 are interposed between two wave sources 122, preferably at equal distances. Therefore, sensors 122, 124 define, on scanning area 120a, a "linear" scanning unit 125a that is substantially elongated along a longitudinal axis 127 thereof. In the embodiment of FIG. 1B, a row of wave sources 122 is disposed directly above a second row of wave detectors 124 in a substantially parallel fashion, and defines a substantially rectangular or square "areal" scanning unit 125b on scanning area 120b. The embodiment of FIG. 1C includes four parallel rows of sensors in each of which two wave detectors 124 (or sources 122) are interposed between two wave sources 122 (or detectors 124). Sensors 122, 124 form a scanning unit 125c substantially rectangular or square but substantially wider than one 125a of FIG. 1A and larger than one 125b of FIG. 1B. It is noted that, depending on the grouping of the sensors 122, 124, scanning unit 125c of optical probe 120c can define multiple scanning units 125a, 125b which have different configurations. To the contrary, the embodiment in FIG. 1D includes wave detectors 124 disposed around wave sources 122 to define a substantially circular scanning unit 125d on its circular scanning area 120d. It is also appreciated that wave sources 122 and detectors 124 of circular scanning unit 125d may be grouped to define foregoing "linear" scanning units 125a as well as "aerial" scanning units 125b.

The wave sources of the present invention are generally arranged to form optical coupling with the medium and to irradiate electromagnetic waves thereinto. Any wave sources may be employed in the optical imaging systems or optical probes thereof to irradiate electromagnetic waves having pre-selected wavelengths, e.g., in the ranges from 100 nm to 5,000 nm, from 300 nm to 3,000 nm or, in particular, in the "near-infrared" range from 500 nm to 2,500 nm. As will be described below, however, typical wave sources are arranged to irradiate near-infrared electromagnetic waves having wavelengths of about 690 nm or about 830 nm. The wave sources may also irradiate electromagnetic waves having different wave characteristics such as different wavelengths, phase angles, frequencies, amplitudes, harmonics, etc. Alternatively, the wave sources may irradiate electromagnetic waves in which identical, similar or different signal waves are superposed on carrier waves with similar or mutually distinguishable wavelengths, frequencies, phase angles, amplitudes or harmonics. In the embodiments of FIGS. 1A to 1D, each wave source 122 is arranged to irradiate electromagnetic waves having two different wave lengths, e.g., about 660 nm to 720 nm, e.g., 690 nm, and about 810 nm to 850 nm, e.g., 830 nm.

Similarly, the foregoing wave detector is preferably arranged to detect the aforementioned electromagnetic waves and to generate the output signal in response thereto. Any wave detectors may be used in the optical imaging systems or optical probes thereof as long as they have appropriate detection sensitivity to the electromagnetic waves having wavelengths in the foregoing ranges. The wave detector may also be constructed to detect electromagnetic waves which may have any of the foregoing wave characteristics. The wave detector may also detect multiple sets of electromagnetic waves irradiated by multiple wave sources and generate multiple output signals accordingly.

Figure 2B:
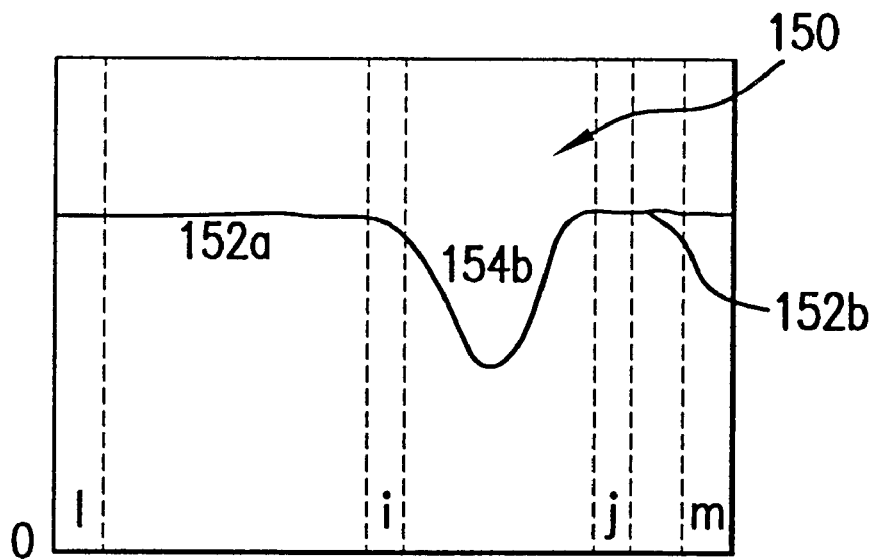

FIGS. 2A and 2B are exemplary output signals generated by the foregoing wave detector(s) according to the present invention. In the figures, the abscissa is an axial distance along an optical probe of the optical imaging system or that along the physiological medium, while the ordinate represents the amplitude of the output signal measured by the wave detector in the target areas of the medium. Each output signal is generally comprised of multiple output value signals or data point signals each corresponding to electromagnetic waves detected by the wave detector of each scanning element of each scanning unit. For illustrative purposes, the target area located at the far-left end of the medium (i.e., adjacent the origin of the figures) is designated as the "first" target area, while the target area at the far right end of the medium as the "last" target area. As illustrated in FIG. 2A, exemplary output signal 150 exhibits relatively flat profile in the first portion or region 152a (i.e., from the first to the i-th target area) and in the second portion or region 152b (i.e., from the j-th to the M-th, last target area). In between flat regions 152a, 152b lies an upright bell-shaped portion 154a (i.e., from the (i+1)-th to the j−1)-th target area) where the amplitudes of output signal 150 vary with respect to the axial position. Output signal 150 of FIG. 2B has a contour similar to that of FIG. 2A, except that an inverted bell-shaped portion 154b (i.e., from the (i+1)-th to the j−1)-th target area) is interposed between two flat portions 152a, 152b.

In a medium composed of a majority of normal tissues, flat portions 152a, 152b of output signal 150 generally correspond to normal cells or tissues and, therefore, constitute a background output signal level for the medium (referred to as a "baseline" of the output signal hereinafter). To the contrary, upright and inverted bell-shaped portions 154a, 154b generally represent abnormal tissues or cells (e.g., tumor tissues, malignant or benign carcinoma such as fiber carcinoma, fluid sacks, and the like) at various development stages. Curved portions 154a, 154b may also represent normal anatomic tissues or cells (e.g., blood vessels, connective tissues, etc.) which have optical properties different from those of the background tissues or cells.

In estimating concentrations of oxygenated and deoxygenated hemoglobins, oxygen saturation, blood volume, and other chromophore properties, there exist needs for calibrating the output signals generated by the wave detectors for initializing the sensors and/or for accounting for the idiosyncratic differences in various scanning elements of the target areas of the medium. Furthermore, signal processing algorithms used in the optical imaging system generally require not the output signals themselves but ratios of the output signals (e.g., optical density) where the output signals are normalized or calibrated by a reference output signal. Accordingly, one aspect of the present invention is to provide an optical imaging system capable of performing self-calibration of the output signals based on the properties of the output signals themselves.

Figure 3:
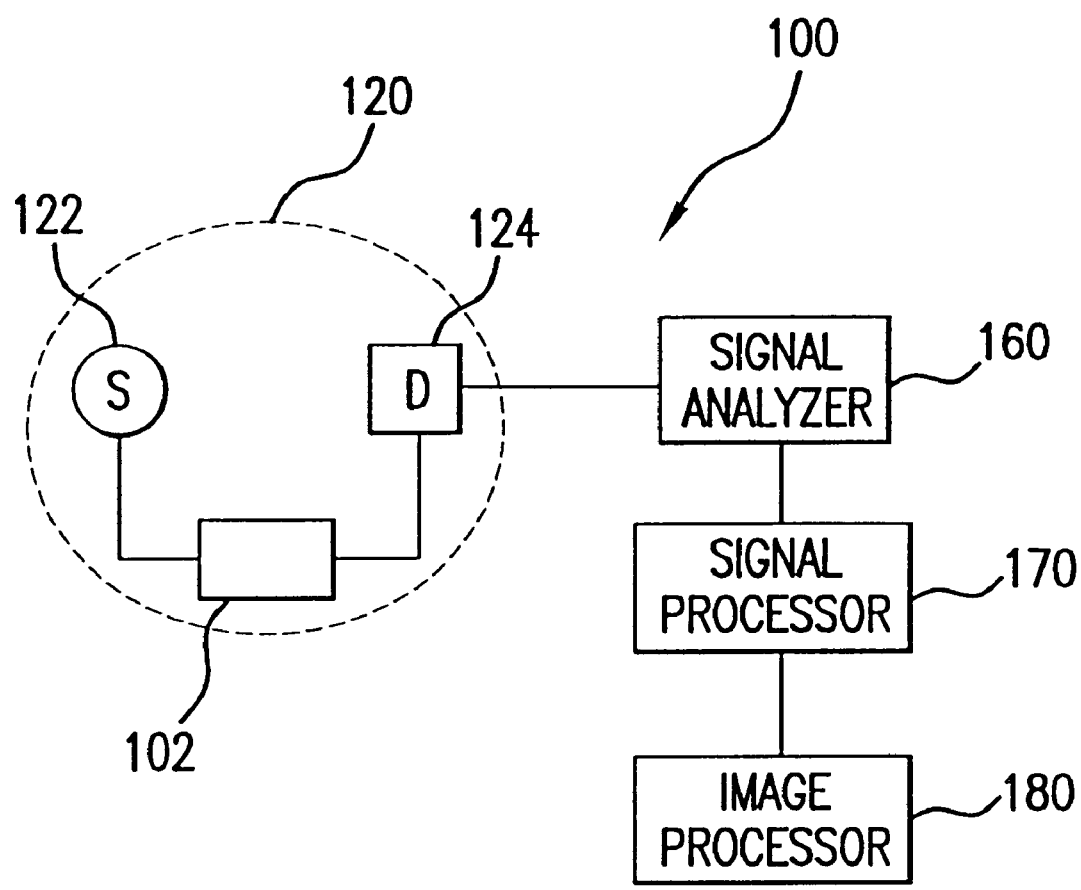
FIG. 3 is a schematic diagram of a typical self-calibrating optical imaging system according to the present invention.

FIG. 3 shows a schematic diagram of an exemplary self-calibrating optical imaging system according to the present invention for generating images of distribution of chromophores or their properties in the target area of a physiological medium. An optical imaging system 100 typically includes at least one wave source 122, at least one wave detector 124, and power source 102. Optical imaging system 100 further includes hardware (circuitry, processors or integrated circuits) or software such as a signal analyzer 160, signal processor 170, and image processor 180, each of which may be operationally coupled to the others and each of which may include one or more functional units.

Signal analyzer 160 operationally couples with one or more sensors 122, 124 so that the signal analyzer can monitor various input and output signals which are required for generating the images of the distribution of the chromophore (or its properties) in the target area of the medium. For example, signal analyzer 160 includes one or more receiving units which operationally couple with wave source 122 and monitor the characteristics of electromagnetic waves irradiated thereby. Each of the receiving units also communicates with wave detector 124 and receives therefrom a first output signal which represents the distribution of the chromophore (or its properties) in a first target area of the medium. The receiving unit may also be arranged to receive external data, operational parameters, and/or other command or control signals supplied by an operator or encoded therein.

Signal analyzer 160 may include other functional units such as a sampling unit, threshold unit, comparison unit, selection unit, etc. The sampling unit receives the foregoing input or output signals or data from the receiving unit and samples the signals at a pre-selected frequency in an analog and/or digital mode. The threshold unit operationally couples with the sampling unit and determines a threshold or cut-off amplitude (or range) which is to be used by the subsequent functional units such as the comparison and selection units. The threshold amplitude or range may be pre-selected and encoded in the threshold unit. The threshold amplitude (or its range) may be manually supplied to the threshold unit by the operator. In the alternative, the threshold amplitude (or its range) may be calculated from the first output signal itself For example, the threshold unit may identify one or more local maximum or minimum amplitudes of the first output signal measured in the first target area, to calculate an average amplitude of at least one or entire portion of such first output signal, to locate a global maximum or minimum amplitude from multiple output signals to be measured in multiple target areas over the medium. After designating such amplitude as a reference amplitude, the threshold unit may calculate the threshold amplitude, e.g., by multiplying the reference amplitude with a pre-selected factor which is generally less than 1.0, by adding thereto or subtracting therefrom another pre-selected factor, by employing a function which yields the threshold amplitude by substituting the foregoing maximum or minimum amplitudes into the function, and the like. The threshold unit may alternatively be encoded with or may include a pre-selected threshold range, receive the range from the operator, or calculate the range based on the foregoing maximum or minimum amplitudes. The comparison unit generally communicates with the threshold unit, receives the threshold amplitude or range therefrom, and compares it with the amplitudes of the first output signal. The selection unit receives the results from the comparison unit and selects multiple points or portions of the first output signal having identical or substantially similar amplitudes. More particularly, when the threshold unit is arranged to provide the threshold amplitude, the selection unit selects the points or portions of the first output signal having amplitudes greater (or less) than the threshold amplitude. However, when the threshold unit provides the threshold range, the selection unit selects multiple points or portions of the first output signal falling within (or outside) the threshold range.

Signal processor 170 operationally couples with signal analyzer 160 and is arranged to "self-calibrate" the first output signal by the first baseline which is obtained from the first output signal itself. Similar to signal analyzer 160, signal processor 170 also includes functional units such as an averaging unit and calibration unit. The averaging unit averages the similar amplitudes of the points or portions of the first output signal selected by the selection unit and designates such average as the baseline of the first output signal. For example, the averaging unit may arithmetically, geometrically, weight- or ensemble-average the similar amplitudes of the foregoing points or portions. Once the first baseline is obtained from the first output signal, the calibration unit normalizes or non-dimensionalizes the first output signal by the first baseline, and provides a self-calibrated first output signal which may be, e.g., a ratio of their amplitudes (i.e., the ratio of the first output signal to its first baseline to yield the optical density signals) or a ratio of their amplitude differences to the first baseline.

Image processor 180 operationally couples with signal processor 170 and is arranged to construct the images of the chromophore (or its properties) based on the self-calibrated first output signal. Typical image processor 180 includes an algorithm unit and an imaging construction unit. The algorithm unit is encoded with or includes at least one solution scheme for solving a set of wave equations applied to wave source(s) 122 and detector(s) 124 arranged according to a pre-selected geometric arrangement. By supplying the algorithm unit with the self-calibrated first output signal along with other requisite initial and/or boundary conditions, the algorithm unit solves the set of the wave equations and provides a set of solutions representing at least one of concentrations of oxygenated or deoxygenated hemoglobins, oxygen saturation, blood volume, other intensive or extensive properties of the chromophores, and the like. The image construction unit then receives the set of solution signals and constructs the images of the spatial distribution of the foregoing properties of the chromophores. If preferred, the image construction unit may be arranged to construct the images regarding the distribution pattern of the first output signal, those of the self-calibrated first output signal itself, and the like.

The foregoing optical imaging systems and methods of the present invention offer several benefits over the prior art optical imaging devices. One of the most serious problems of the prior art devices lies in the fact that their optical probes or sensors require a priori estimation of the baseline of their output signals. For example, the probes or sensors are positioned in a reference medium (e.g., a phantom) or in a reference area of the subject, output signals are generated by the wave detectors, and baselines are estimated based on the optical property of the reference medium or area. The probes or sensors are then moved and placed on the target area of the subject to be scanned thereby. It is well known in the field that such calibration method constitutes a major source of error in the resulting signals due to possible inherent differences in optical properties between the target area and reference medium or area. In addition, repositioning the probes or sensors from the reference area to the target area frequently results in inconsistent optical coupling between the sensors and target area and between the sensors and reference medium (or area), thereby introducing additional noises thereto. The optical imaging system of the present invention, however, allows the operator to obtain the first output signal and first baseline thereof from the same target area without moving and/or repositioning the optical probes or sensors from the first target area. Because the foregoing optical imaging system obtains the baseline from the same target area of the same medium under the identical optical coupling (therefore referred to as "self-calibration"), the optical imaging system of the present invention obviates the need for such reference measurement and, thus, eliminates the error associated with the inconsistent optical coupling. In addition, because the foregoing optical imaging systems can estimate the first output signal and its baseline from the same target area, such optical imaging system provides more accurate and reliable results. Furthermore, due to the simple data processing algorithms for estimating such baseline, the foregoing optical imaging system allows construction of the images of the chromophore properties on a substantially real-time basis.

The foregoing optical imaging systems and methods thereof may be modified in various aspects without departing from the scope of the present invention.

First of all, it is appreciated that the exact number of the wave sources and detectors and geometric arrangements therebetween are not critical in realizing the present invention described herein. Accordingly, virtually any number of wave sources and wave detectors may be implemented into the optical probe of the optical imaging system in any geometric arrangements. The self-calibrating feature of the present invention then applies to each scanning element formed by each pair of the wave source and detector which may irradiate multiple sets of electromagnetic waves having, e.g., different wave characteristics, identical or different signal waves superposed on different or identical carrier waves, and the like. The wave sources may also be arranged to irradiate such electromagnetic waves continuously, periodically or intermittently.

As discussed in the co-pending '972 application, it is generally preferred, however, that the wave sources and detectors be arranged according to a few semi-empirical design rules which are expected to enhance accuracy, reliability, and/or reproducibility of the signal baselines as well as the estimated absolute values of the chromophore properties. Such exemplary design rules are: (1) the scanning unit preferably includes at least two wave sources and at least two wave detectors; and (2) the distances between any wave source and wave detector within a scanning unit do not exceed a threshold sensitivity range of the wave detector which may range from, e.g., several to 10 cm or, in particular, about 5 cm for most human and/or animal tissues. Furthermore, the wave sources and detectors are preferably arranged to define the scanning units having continuous scanning area throughout the entire region thereof so that a single measurement by the scanning unit can generate the output signal covering the entire scanning area. For this purpose, the wave sources and detectors may be spaced at distances no greater than a threshold distance thereof. Selection of the optimal spacing between the wave sources and detectors is generally a matter of choice of one of ordinary skill in the art and such spacing is determined by many factors including, e.g., optical properties of the medium (e.g., absorption coefficient, scattering coefficient, and the like), irradiation or emission capacity of the wave sources, detection sensitivity of the wave detectors, configuration of the scanning elements and units, number of the wave sources and/or detectors in the optical probe, geometric arrangement between the wave sources and detectors, grouping of the wave sources and detectors in each of the scanning elements and each of the scanning units, and so on.

The optical imaging system may include a filter unit to improve a signal-to-noise ratio of the output signals as well as that of subsequent signals including the baselines and self-calibrated output signals. Accordingly, the filter unit is preferably arranged to treat the output signals before they are processed by the signal analyzer and processor. When a single output signal is obtained for each target area (or medium), the filter unit preferably includes a low pass filter which may remove high-frequency noises from the output signals. When the optical probe is arranged to generate multiple output signals from a single target area, however, their signal-to-noise ratios may also be improved through various averaging methods, e.g., by arithmetically or geometrically averaging such multiple output signals. In addition, the filter unit may also weight-average or ensemble-average the foregoing output signals. Such filtering operation can be performed in an analog and/or digital mode.

The optical imaging system may also include a spline unit for smoothing out abrupt changes or jumps in the amplitudes of adjacent portions or data points of the output signal(s). Accordingly, the spline unit may include an interpolation algorithm or equivalent circuitry or software.

The foregoing signal analyzer and signal processor of the present invention are preferably arranged to operate on a substantially real-time basis. For example, once the optical probe is positioned in the first target area and the wave detector generates the first output signal, the signal analyzer identifies the portions of the first output signal having similar amplitudes and the signal processor provides the self-calibrated first output signal before the optical probe is moved to or repositioned in the adjacent target area. The image processor may also be arranged to provide requisite images before moving the optical probe to other target areas as well. Therefore, the optical imaging system of the present invention can generate the images of two- and/or three-dimensional distribution of the chromophores or their properties on a substantially real time basis.

The signal analyzer of the present invention may also be arranged to identify different points or portions of the output signals using various algorithms different from the one disclosed hereinabove. For example, instead of focusing only on amplitudes of output signals, the signal analyzer may calculate and assess other features of the output signals, e.g., curvature of the output signals which may be signified by their first derivative values (or slopes), concaveness or convexity of the output signals assessed by the values of their second derivatives, number and locations of local maximums or minimums, and the like. For example, when the output signal shows a slight increase or decrease, identification of such point of deflection may be facilitated by analyzing the first and/or second derivative values of the output signal. In addition, by considering these secondary parameters along with the amplitudes of the output signals, different portions or segments may be identified along the output signal where each portion or segment exhibits different profiles (e.g., flat, sloped, convex or concave).

In general, portions of the output signal with a substantially flat profile and similar amplitudes indicate that the region of the target area representing such portions of the output signal is predominantly composed of a homogeneous material such as normal tissues and cells. To the contrary, portions of the output signal having curved profile and varying amplitudes generally imply that the regions of the target area corresponding to such portions have optical properties different from those of the background of the medium such as the normal tissues or cells. Accordingly, such regions are more likely than not to include abnormal cells, although it may also be possible that they merely reflect normal connective structure or neurovascular tissues. Identification of a demarcation between such normal and abnormal regions may be facilitated by analyzing the first and/or second derivatives of the output signal as well.

The signal analyzer of the optical imaging system of the present invention is arranged to identify flat (or linear) portions of the output signal or, conversely, the rest of the output signal, i.e., non-flat or curved portions. As discussed above, the signal analyzer may compare amplitudes of each point of the output signal with the threshold amplitude or range. Alternatively, the signal analyzer may divide the output signal into multiple shorter segments, obtain average amplitudes for individual segments, and compare such averages with the threshold amplitude or range which in turn may be a local or global maximum or minimum amplitude thereof. Regardless of the nature of the threshold value, however, the output signal may vary in its amplitudes in the flat as well as non-flat portions. Thus, the signal analyzer may be provided with a secondary cut-off amplitude or a cut-off range of deviation so that any points of the output signal not satisfying the cut-off threshold values may not be included in the flat or non-flat portions.

In order to ensure accuracy of a baseline of the output signal obtained from a specific target area of the medium, other baselines may be obtained from neighboring target areas and compared with the baseline from the specific target area. The self-calibrating optical imaging system of the present invention accomplishes this objective by providing algorithms and methods for determining a composite baseline when the baselines obtained from different target areas are not substantially identical throughout the medium.

Figure 4A:
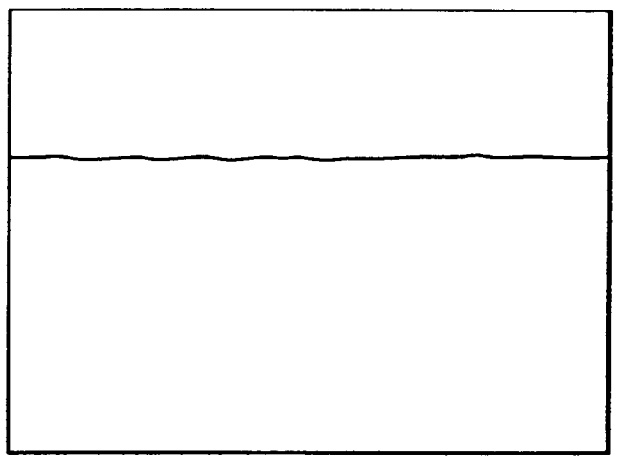
FIGS. 4A to 4C are further exemplary output signals generated by wave detectors according to the present invention.
Figure 4B:
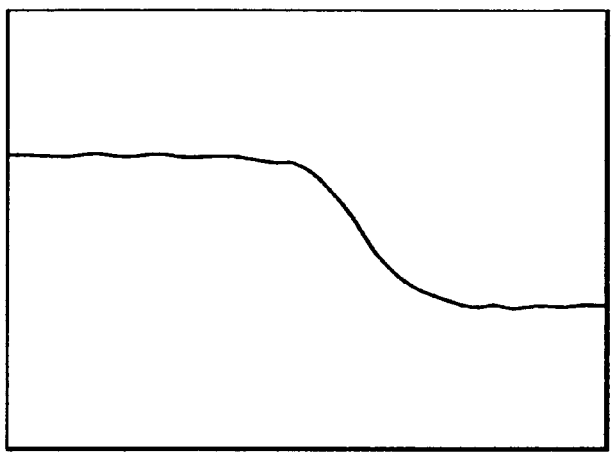
Figure 4C:
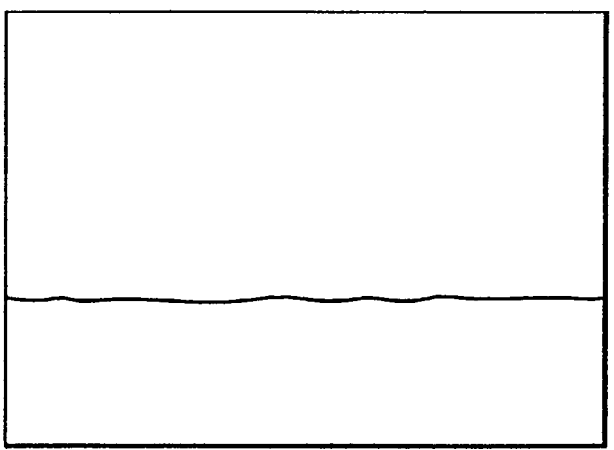

FIGS. 4A to 4C are further exemplary output signals generated by wave detectors according to the present invention, where each figure represents the output signal obtained from the first, second, and third target area, respectively, and where each target area is covered by multiple scanning elements and scanning units. As shown in the figures, the output signals of FIGS. 4A and 4C have different amplitudes but flat profiles in the first and third target areas, respectively, whereas the output signal of FIG. 4B decreases along the axial direction in the second target area. When the amplitudes of the output signal of FIG. 4A are not substantially different from those of FIG. 4C or the differences therebetween are within a pre-selected tolerance range, the data points of the output signals in FIGS. 4A to 4C may be averaged to yield the baseline of the medium. However, when such differences are not negligible, FIGS. 4A and 4C manifest that one of the first and third target areas may be mainly comprised of the normal tissues or cells and the output signal therefrom represents a background output signal of the medium, whereas the other of the two target areas may be composed of the abnormal tissues or cells and, thus, its output signal is skewed or biased upward or downward due to the presence of abnormal cells, tissues or lumps having a size enough to cover the entire first or third target area. In case the signal analyzer should be provided with a threshold amplitude or range supplied by the operator, the signal analyzer compares the data points of the target areas and locates the selected portion(s) of the output signal to be used for estimating the baseline. However, when the signal analyzer identifies the selected portions adaptively from the output signals themselves (e.g., by identifying the local or global maximum or minimums and calculating the threshold amplitudes or ranges accordingly), the signal analyzer may have to discern which data points should be used for calculating the baseline of the medium. In one embodiment, the baselines may be obtained from the adjacent target areas and compared with the baseline obtained from FIGS. 4A and 4C. When the region of higher (or lower) amplitudes is constrained to one area while the region of lower (or higher) amplitudes tends to surround the constrained area, the region with the lower (or higher) amplitudes is more likely to be the background normal tissues or cells, whereas the region having higher (or lower) amplitudes is more likely to include the abnormal tissues, cells or lumps. Alternatively, the signal analyzer may supply the operator with different amplitude values and allow the operator to manually select the normal and/or abnormal region.

In some cases, output signals obtained from multiple different target areas may yield similar but not identical baselines. The signal analyzer may then be arranged to obtain a composite or average baseline from multiple baselines and utilize that composite baseline to normalize the output signals obtained from all target areas of the medium. As discussed above, such multiple baselines may be arithmetically, geometrically, weight- or ensemble-averaged. Alternatively, the signal analyzer may allow the operator to select a single baseline and to designate it as the composite baseline. Alternatively, each output signal (or a group thereof) may be normalized by the baseline calculated therefrom. When the signal processor generates the self-calibrated signals and the image processor constructs multiple local images (e.g., one per each scanning area or target area), a composite image may be made from multiple local images based on the individual baselines used in each target area (or a group thereof). This embodiment proves to be advantageous particularly when the physiological medium includes various anatomical structures having different optical properties. For example, the self-calibrating optical imaging system may scan the brain to detect potential or actual stroke conditions. Brain tissues and surrounding skull normally exhibit at least minimally different optical characteristics, and the thickness of the skull may vary in different parts of the brain. When the composite baseline is calculated from multiple baselines and used to normalize the output signals measured from different parts of the brain, all image pixels will have the same extent of normalization, i.e., identical brightness-scale or color-scale across the entire medium. Although such images with the uniform background level may assist a physician in making a comparative diagnosis, he or she may not be able to locate a mild stroke condition when it is overshadowed in a target area that is normalized by a baseline having a higher amplitude. To the contrary, when the images are constructed from the self-calibrated output signals based on individual baselines, each target area may have its own brightness-scale or color-scale. Thus, the mild stroke condition may not necessarily be compromised in the image but the physician may have to analyze each image separately. One way of obviating such inconvenience is to artificially enhance the contrast between the background anatomical structure and abnormal tissues included in each target area. For example, upon identifying any possible abnormalities, the imaging member may identify the demarcation line and augment the signals corresponding to the demarcation line and/or the abnormalities such that the amplified signals will not be overshadowed by the color-scale or brightness-scale of the images based on the composite baseline. A special marker or color may also be added to such enhanced signal to alarm the physician as well.

It is appreciated that the foregoing arrangement of the optical imaging system of the present invention may be modified without departing from the scope of the invention. For example, the foregoing functional units of the signal analyzer, the signal processor, and the image processor may be further differentiated or combined or may be implemented into another portion of the optical imaging system. Such functional units may also be arranged to form different operational connection therebetween. For example, the receiving unit and sampling unit of the signal analyzer may be combined. Similarly, the comparison unit and selection unit of the signal analyzer may also be combined. The image processor may be arranged to operationally communicate with such units of the signal analyzer as well.

The foregoing self-calibrating optical imaging systems and methods of the present invention may also be used to provide temporal changes in blood or fluid volume in the target area of the medium. As discussed in the co-pending application entitled "Optical Imaging System with Movable Scanning Unit," the concentrations of the oxygenated and deoxygenated hemoglobins are calculated according to one of the algorithms disclosed in the co-pending '972 application. Once such concentrations are obtained, their sum (i.e., total hemoglobin concentration) is also obtained. By sampling the output signals from the wave detectors positioned in the target area over time, changes in the total hemoglobin concentration is obtained. By assuming that blood hematocrit (i.e., the volume percentage of the red blood cells in blood) is maintained constant over time for blood flowing through the target area, temporal changes in the blood volume in such target area may be directly calculated in terms of temporal changes of hematocrit of the target area. In such cases, the optical imaging system may calculate the baseline of the output signal and provide the self-calibrated output signal as discussed above. Alternatively, the optical imaging system may also calculate multiple baselines from the same target area over time, obtain a temporally-averaged composite baseline, and provide a temporally-compensated self-calibrated output signal.

Although the foregoing disclosure of the present invention is mainly directed to self-calibration of optical imaging systems for providing images of the spatial distribution of the chromophore property, the present invention may also be applied to optical imaging systems for generating the images of temporal distribution thereof. For example, the optical probe may be arranged to scan a specific target area over time. From the variations in the output signals detected over different intervals in the target area, the signal analyzer and processor can establish the baseline and provide the self-calibrated first output signals over time. The image processor then constructs frames of images representing temporal changes in the chromophore property of the target area. Alternatively, the optical imaging system can also provide temporally-averaged baseline and temporally-compensated self-calibrated output signal as described in the foregoing paragraph. It is noted that the temporal changes of the chromophore properties usually relate to the relative values and, thus, do not directly provide any absolute values thereof. However, once an absolute value of such property is determined at any reference time frame, preceding or subsequent changes of such property may readily be converted to the absolute values by successively calculating the absolute values forwardly or backwardly.

The self-calibrating arrangements and methods of the present invention may be used in optical imaging systems for obtaining images of three-dimensional distribution of the chromophore in the physiological medium. As discussed above, electromagnetic waves irradiated by the wave source are traveling through a target volume defined by a target area and by a pre-selected depth or thickness of the medium. Therefore, the wave detectors can generate multiple output signals each carrying optical information of a specific target layer of the medium. Once such output signals are obtained, a baseline can be estimated by the foregoing algorithms described herein. For example, a single baseline can be designated to the entire target volume. In the alternative, multiple baselines may be preferably defined at each depths or layers of the target volume. In case multiple baselines should be used, these baselines may be averaged or normalized with respect to each other so that resulting three-dimensional images may be constructed under a uniform gray-scale or color-grade.

Though any analytical or numerical schemes may be used to obtain solutions of the wave equations, an exemplary algorithm unit of the invention preferably incorporates solution schemes disclosed in the co-pending '972 application. For example, the absolute values of concentration of deoxygenated hemoglobin, [Hb], concentration of oxygenated hemoglobin, [HbO], and oxygen saturation, $SO_2$, are obtained by equations (8a) to (8d) and (9b) of the co-pending '972 application, respectively. In the alternative, the algorithm unit may also employ the over-determined iterative method as disclosed in the foregoing '972 application, where the absolute values of [Hb], [HbO], and $SO_2$ are determined by equations (17a) to (17c) of the co-pending '972 application, respectively. In yet another alternative, changes in the chromophore properties are determined by estimating changes in optical characteristics of the target area of the medium. For example, changes in concentrations of oxygenated and deoxygenated hemoglobins may be calculated from the differences in their extinction coefficients which are in turn measured by electromagnetic waves having two different wavelengths. In an exemplary numerical scheme, the photon diffusion equations are modified based on the diffusion approximation described in, e.g., Keijer et al., "Optical Diffusion in Layered Media," *Applied Optics*, 27, p. 1820–1824 (1988), and Haskell et al., "Boundary Conditions for Diffusion Equation in Radiative Transfer," *Journal of Optical Society of America*, A, 11, p.2727–2741, 1994. Details of the foregoing scheme is also provided in the co-pending '972 application. In each of these schemes, the output signals are calibrated by their baselines obtained by one of the foregoing methods.

The wave sources and detectors of the optical probe of the optical imaging system of the present invention may be arranged to satisfy an embodiment disclosed in the co-pending '972 application, i.e., the wave sources and detectors are arranged to have substantially identical near- and far-distances therebetween. For example, in scanning units 125a, 125b of FIGS. 1A and 1B, a first near-distance between a first wave source and a first wave detector is substantially identical to a second near-distance between a second wave source and a second wave detector. In addition, a first far-distance between the first wave source and the second wave detector is substantially identical to a second far-distance between the second wave source and a first wave detector. A major advantage of such symmetric arrangement is that electromagnetic waves irradiated by the wave sources are substantially uniformly transmitted, absorbed, and/or scattered throughout the entire area or volume of the medium scanned by the scanning unit. Accordingly, such scanning unit can provide uniform coverage of the target area of the medium and, therefore, enhance accuracy and reliability of the output signal (e.g., an improved signal-to-noise ratio) generated by the wave detector.

The foregoing self-calibrating optical imaging systems, optical probes, and methods of the present invention can be used in both non-invasive and invasive procedures. For example, the foregoing self-calibrating optical probes may be non-invasively disposed on the target area on an external surface of the test subject. Alternatively, a miniaturized self-calibrating optical probe may be implemented in a tip of a catheter which is invasively disposed on an internal target area of the subject. The foregoing optical imaging systems and optical probes may also be used to determine intensive properties of the chromophores such as concentrations, sums of or differences in concentrations, and/or ratios thereof. The foregoing optical imaging systems and probes may further be utilized to calculate extensive chromophore properties such as volume, mass, volume, volumetric flow rate or mass flow rate. As discussed above, such chromophores may include, e.g., solvents of the medium, solutes dissolved in the medium, and/or other substances included in the medium, each of which interacts with electromagnetic waves transmitted through the medium. Examples of the chromophores may include, but not limited to, cytochromes, hormones, enzymes, both neuro- and chemo-transmitters, proteins, cholesterols, apoproteins, lipids, carbohydrates, cytosomes, blood cells, cytosols, oxyygenated hemoglobin, deoxygenated hemoglobin, and water. Specific examples of the chromophore properties may include, but not limited to, concentrations of oxygenated and deoxygenated hemoglobins, oxygen saturation, and blood volume.

It is appreciated that the foregoing optical imaging systems, optical probes thereof, and methods therefore may be readily adjusted to provide images of distribution of different chromophores or properties thereof. Because different chromophores generally respond to electromagnetic waves having different wavelengths, the wave sources of such optical imaging systems and probes may be manipulated to irradiate electromagnetic waves interacting with pre-selected chromophores. For example, the near-infrared waves having wavelengths between 600 nm and 1,000 nm, e.g., about 690 nm and 830 nm are suitable to measure the distribution pattern of the hemoglobins and their property. However, the near-infrared waves having wavelengths between 800 nm and 1,000 nm, e.g., about 900 nm, can also be used to measure the distribution pattern of water in the medium. Selection of an optimal wavelength for detecting a particular chromophore generally depends on optical absorption and/or scattering properties of the chromophore, operational characteristics of the wave sources and/or detectors, and the like.

The foregoing optical imaging systems, optical probes, and methods of the present invention may be clinically applied to detect tumors or stroke conditions in human breasts, brains, and any other areas of the human body where the foregoing optical imaging methods such as diffuse optical tomography is applicable. The foregoing optical imaging systems and methods may also be applied to assess blood flow into and out of transplanted organs or extremities and/or autografted or allografted body parts or tissues. The foregoing optical imaging systems and methods may be arranged to substitute, e.g., ultrasonogram, X-rays, EEG, and laser-acoustic diagnostic. Furthermore, such optical imaging systems and methods may be modified to be applicable to various physiological media with complicated photon diffusion and/or with non-flat external surface.

It is noted that the optical imaging systems, optical probes, and methods of the present invention may incorporate and/or applied to related inventions and embodiments thereof disclosed in the commonly assigned co-pending U.S. application Ser. No. (N/A), entitled "Optical Imaging System with Movable Scanning Unit," another commonly assigned co-pending U.S. application Ser. No. (N/A), entitled "Optical Imaging System for Direct Image Construction," and yet another commonly assigned co-pending U.S. application Ser. No. (N/A), "Optical Imaging System with Symmetric Optical Probe," all of which have been filed on Feb. 6, 2001 and all of which are incorporated herein in their entirety by reference.

Following example describes an exemplary optical imaging system, optical probe, and methods thereof according to the present invention. The results indicated that the foregoing exemplary optical imaging system provided reliable and accurate images of two-dimensional distribution of the blood volume and the oxygen saturation in the target areas of the human breast tissues.

EXAMPLE

Figure 5:
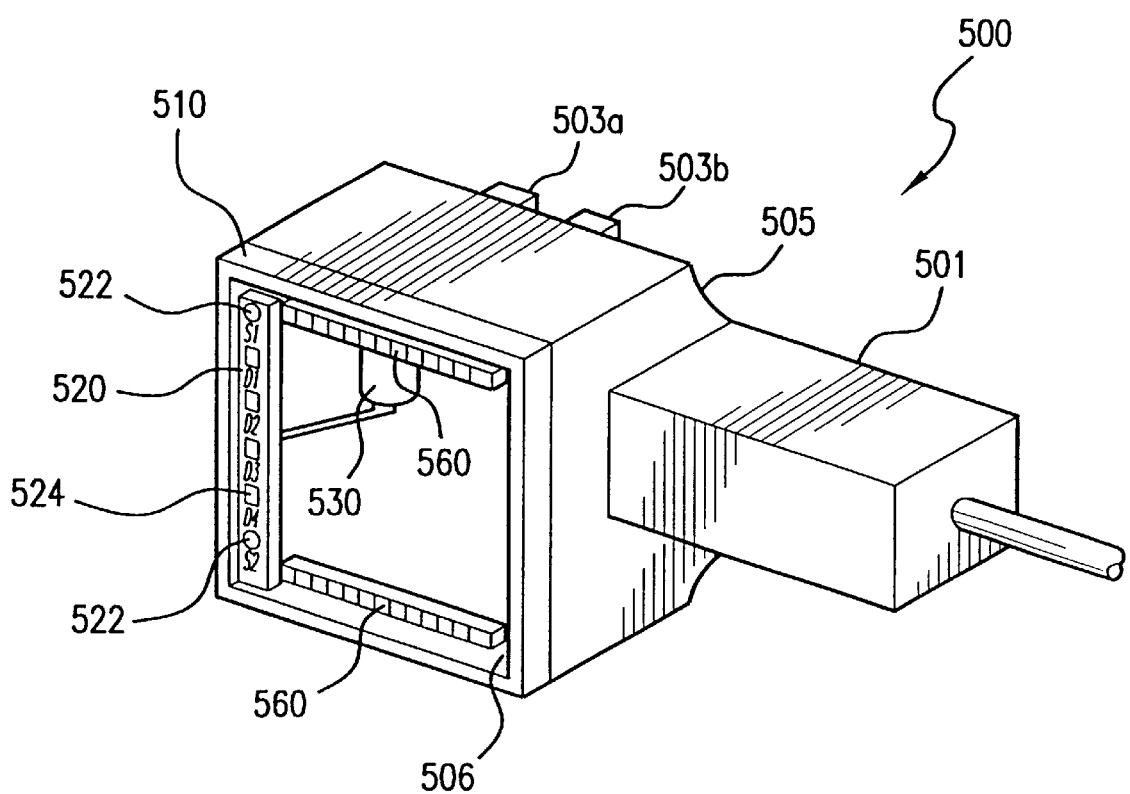
FIG. 5 is a schematic view of another exemplary optical imaging system according to the present invention.

An exemplary optical imaging system 500 was constructed to obtain images of two-dimensional distribution of blood volume and oxygen saturation in target areas of female human breasts. FIG. 5 is a schematic diagram of a prototype optical imaging system according to the present invention.

Prototype optical imaging system 500 typically included a handle 501 and a main housing 505. Handle 501 was made of poly-vinylchloride (PVC) and acrylic stock, and provided with two control switches 503a, 503b for controlling operations of various components of system 500. Main housing 505 included a body 510, a movable member 520, an actuator member 530, an imaging member (not shown), and a pair of guiding tracks 560.

Body 510 was shaped as a substantially square block (3.075"×2.8"×2.63") and provided with barriers along its sides. Body 510 was arranged to movably couple with rectangular movable member 520 (1.5"×2.8"×1.05") designed to linearly translate along a path substantially parallel with one side of body 510.

Movable member 520 included two wave sources 522, $S_1$ and $S_2$, each of which was capable of irradiating electromagnetic waves having different wavelengths. In particular, each wave source 522 included two laser diodes, HL8325G and HL6738MG (ThorLabs, Inc., Newton, N.J.), where each laser diode irradiated the electromagnetic waves with wavelengths of 690 nm and 830 nm, respectively. Movable member 520 also included four identical wave detectors 524 such as photo-diodes $D_1$, $D_2$, $D_3$, and $D_4$, (OPT202, Burr-Brown, Tucson, Ariz.) which were interposed substantially linearly between wave sources 522. Wave sources 522 and detectors 524 were spaced at identical distances such that the foregoing sensors 522, 524 satisfy the foregoing symmetry requirements of the co-pending '972 application.

Actuator member 530 included a high-resolution linear-actuating-type stepper motor (Model 26000, Haydon Switch and Instrument, Inc., Waterbury, Conn.) and a motor controller (Spectrum PN 42103, Haydon Switch and Instrument, Inc.). Actuator member 530 was mounted on body 510 and engaged with movable member 520 so as to linearly translate movable member 520 along guiding tracks 560 fixedly positioned along the linear path. A pair of precision guides (Model 6725K11, McMaster-Carr Supply, Santa Fe Springs, Calif.) was used as guiding tracks 560.

The imaging member was provided inside handle 501 and included a data acquisition card (DAQCARD 1200, National Instruments, Austin, Tex.). Main housing 505 was made of acrylic stocks and constructed to open at its front face. Perspex Non-Glare Acrylic Sheet (Liard Plastics, Santa Clara, Calif.) was installed on a front face 506 of housing 505 and used as a protective screen to protect wave sources 522 and detectors 524 from mechanical damages.

In operation, movable member 520 was positioned in its starting position, i.e., the far-left side of body 505. An operator turned on the main power of system 500 and tuned wave sources 522 and detectors 524 by running scanning system software. A breast of a human subject was prepped and body 505 was positioned on the breast so that sensors 522, 524 of movable member 520 were placed in a first target area of the breast and formed appropriate optical coupling therewith. The first target area was scanned by clicking one control switch 503a on handle 501. Actuator member 530 translated movable member 520 linearly along one side of body 510 along guide tracks 560.

Wave sources 522 were synchronized to ignite their laser diodes in a pre-selected sequence. For example, a first laser diode of the wave source, $S_1$, was arranged to irradiate electromagnetic waves of wavelength 690 nm and wave detectors 524 detected the waves and generated a first set of output signals in response thereto. During the foregoing irradiation and detection period which generally lasted about 1 msec (with duty cycle from 1:10 to 1:1,000), all other laser diodes were turned off to minimize interference noises. After completing the irradiation and detection, the first laser diode of the wave source, $S_1$, was turned off and the first laser diode of the wave source, $S_2$, was turned on to irradiate electromagnetic waves of the same wavelength, 690 nm. Wave detectors 524 detected the waves and generated a second set of output signals accordingly. Other laser diodes were maintained at off positions during the foregoing irradiation and detection period as well. Similar procedures were repeated to the second laser diodes of the wave sources, $S_1$ and $S_2$, where both second laser diodes were arranged to sequentially irradiate the electromagnetic waves having wavelengths 830 nm.

The imaging member was also synchronized with wave sources 522 and detectors 524 and sampled the foregoing sets of output signals in a pre-selected sampling rate. In particular, the imaging member was arranged to process such output signals by defining a first and second scanning units, where the first scanning unit was comprised of the wave sources, $S_1$ and $S_2$, and the wave detectors, $D_1$ and $D_4$, and the second scanning unit was made up of the wave sources, $S_1$ and $S_2$, and the wave detectors, $D_2$ and $D_3$. Both of the first and second scanning units had the source-detector arrangement which satisfied the symmetry requirements of the co-pending '972 application. Therefore, concentrations of the oxygenated and deoxygenated hemoglobins were obtained by the equations (1a) to (1e), and the oxygen saturation, $SO_2$, by the equation (1e). Furthermore, relative values of blood volume (i.e., temporal changes thereof) was calculated by assessing the changes in hematocrit in the target areas as discussed above.

Actuator member 530 was also synchronized with the foregoing irradiation and detection procedures so that wave sources 522 and detectors 524 scanned the entire target area (i.e., irradiating electromagnetic waves thereinto, detecting such therefrom, and generating the output signals) before they were moved to the next adjacent region of the target area by actuator member 530. When movable member 520 reached the opposing end of body 510, actuator member 530 translated movable member 520 linearly to its starting position. The foregoing irradiation and detection procedures were repeated during such backward linear movement of movable member 520 as well. After the scanning procedure was completed, the operator pushed the other control switch 503b to send a signal to the imaging member which started image construction process and provided two-dimensional images of spatial distribution of the oxygen saturation in the target area and the temporal changes in the blood volume therein.

Figure 6A:
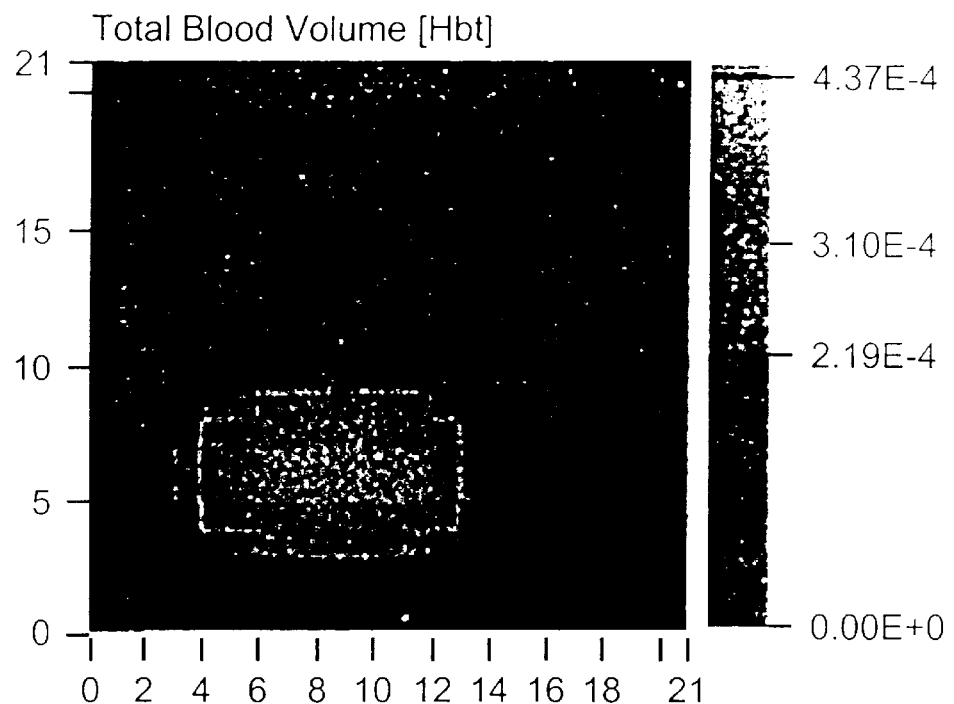
FIGS. 6A and 6B are images of changes in blood volume in both normal and abnormal breast tissues, respectively, measured by the optical imaging system of FIG. 5 according to the present invention.
Figure 6B:
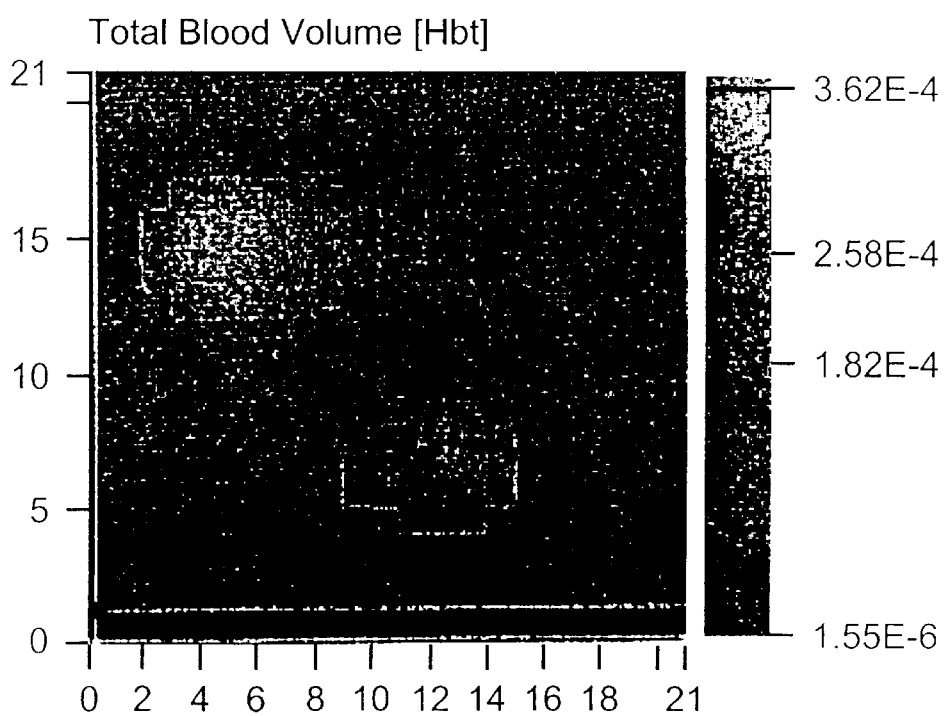
Figure 7A:
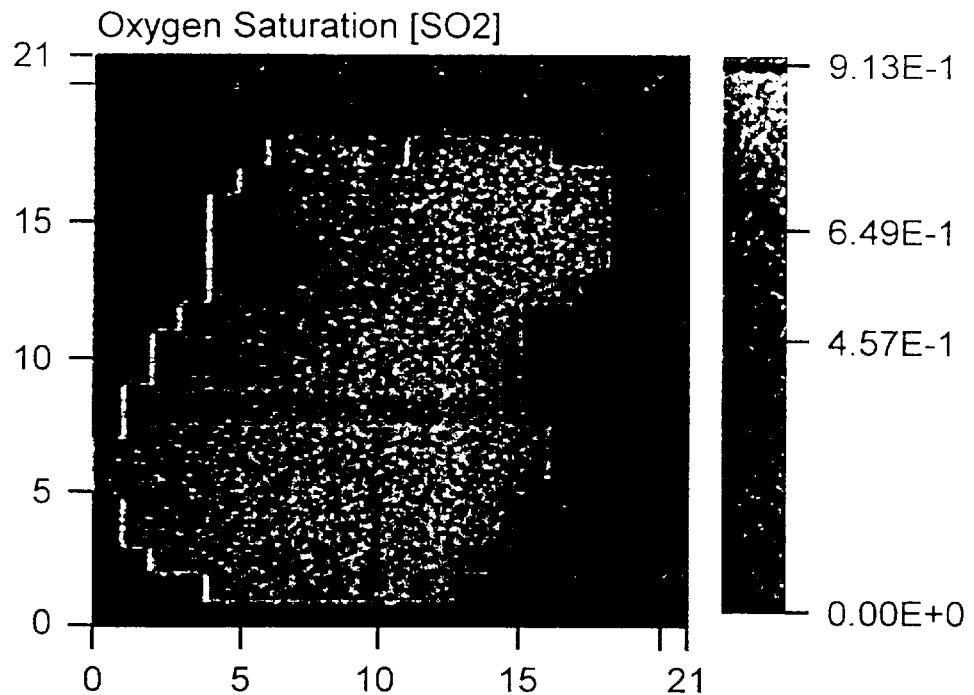
FIGS. 7A and 7B are images of oxygen saturation in normal and abnormal breast tissues, respectively, measured by the optical imaging system of FIG. 5 according to the present invention.
Figure 7B:
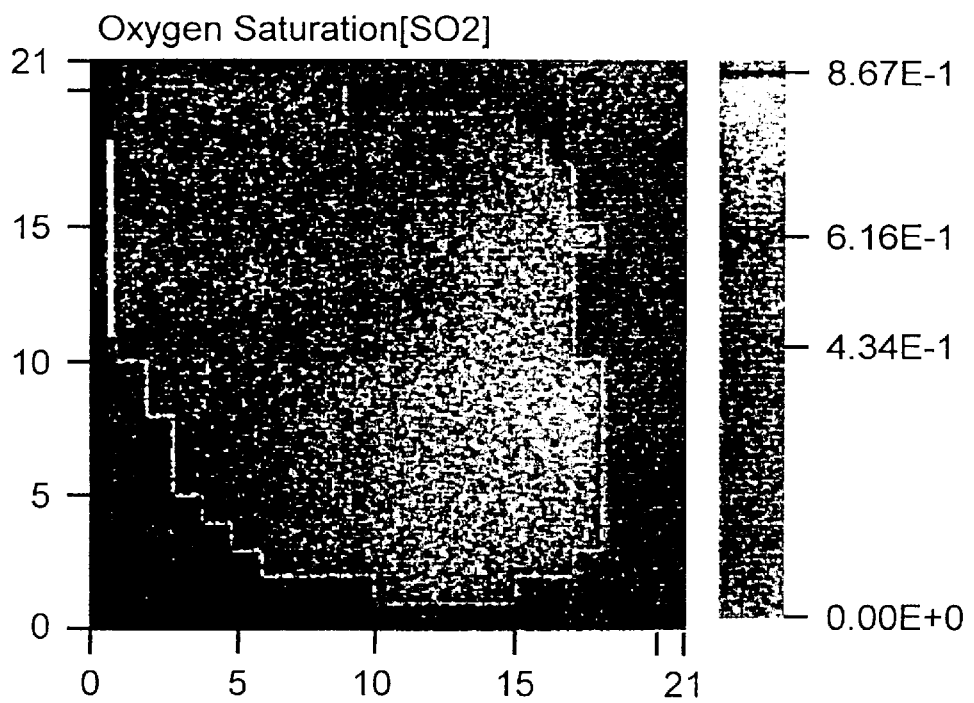

FIGS. 6A and 6B are two-dimensional images of blood volume in normal and abnormal breast tissues, respectively, both measured by the optical imaging system of FIG. 5. In addition, FIGS. 7A and 7B are two-dimensional images of oxygen saturation in normal and abnormal breast tissues, respectively, both measured by the optical imaging system of FIG. 5 according to the present invention. As shown in the figures, the optical imaging system provided that normal tissues had the higher oxygen saturation (e.g., over 70%) in the area with the maximum blood volume. However, the higher oxygen saturation in the corresponding area of the abnormal tissues was as low as 60%.

It is to be understood that, while various embodiments of the invention has been described in conjunction with the detailed description thereof, the foregoing is only intended to illustrate and not to limit the scope of the invention, which is defined by the scope of the appended claims. Other related embodiments, aspects, advantages, and/or modifications are within the scope of the following claims.

What is claimed is:

1. An optical imaging system for generating images of target areas of a physiological medium, said images representing distribution of hemoglobins in said target areas, said system comprising:
   an optical probe having a wave source and a wave detector, wherein said wave source is configured to irradiate near-infrared electromagnetic waves into a first target area of said physiological medium and wherein said wave detector is configured to detect said near-infrared electromagnetic waves from said first target area of said medium and to generate a first output signal in response thereto;
   a signal analyzer configured to receive said first output signal, to analyze amplitudes of said first output signal, and to select a plurality of points of said first output signal having substantially similar amplitudes; and
   a signal processor configured to calculate a first baseline from said first output signal and to provide a self-calibrated first output signal by manipulating both of said first output signal and its first baseline, wherein said first baseline is a representative amplitude of said similar amplitudes.

2. The system of claim 1 wherein said optical probe includes a two or more wave sources and two or more wave detectors and defines a scanning area therearound, which scanning area is a substantial portion of said first target area.

3. The system of claim 1 wherein said optical probe includes two or more wave sources and two or more wave detectors and defines a scanning unit forming a scanning area therearound, which is a fraction of said first target area.

4. The system of claim 3 wherein said optical probe has an actuator and a housing, said actuator configured to move at least one of said wave source and detector across a plurality of regions of said first target area while said housing of said optical probe is positioned in said first target area.

5. The system of claim 4 wherein at least one of said wave detectors is configured to generate a plurality of said first output signals in said regions of said first target area.

6. The system of claim 1 wherein said signal processor is configured to provide said self-calibrated first output signal on a substantially real-time basis.

7. The system of claim 1 further comprising:
   an image processor configured to construct said images of said distribution of hemoglobins in said first target area from said self-calibrated first output signals.

8. The system of claim 7 wherein said image processor is configured to construct said images on a substantially real-time basis.

9. The system of claim 7 wherein said hemoglobins in said first target area are at least one of oxygenated hemoglobin and deoxygenated hemoglobin.

10. The system of claim 7 wherein said images relate to said distribution of at least one of oxygen saturation, concentration of oxygenated hemoglobin, concentration of deoxygenated hemoglobin, blood volume, and changes in blood volume in said first target area, wherein said oxygen saturation is defined as a ratio of said concentration of oxygenated hemoglobin to a sum of said concentrations of oxygenated and deoxygenated hemoglobins.

11. The system of claim 1 wherein said distribution includes at least one of spatial distribution of hemoglobins in said first target area and temporal changes in said distribution of hemoglobins in said first target area over time.

12. The system of claim 1 further comprising:
   a memory unit configured to store at least one of said first output signal, first baseline, and self-calibrated first output signal.

13. The system of claim 1 wherein said signal analyzer includes:
   a threshold unit for providing a threshold amplitude;
   a comparison unit for comparing said amplitudes of said first output signal with said threshold amplitude; and
   a selection unit for identifying said plurality of said points of said first output signal having substantially similar amplitudes.

14. The system of claim 13 wherein said threshold unit is configured to receive said threshold amplitude from an operator.

15. The system of claim 13 wherein said threshold unit is configured to calculate a reference amplitude from said first output signal and to calculate said threshold amplitude from said reference amplitude.

16. The system of claim 15 wherein said reference amplitude is calculated from at least one of:
   a local maximum of said first output signal from said first target area;
   a local minimum of said first output signal from said first target area;
   an average of at least a portion of said first output signal;
   a global maximum of a plurality of said output signals from a plurality of said target areas of said medium;
   a global minimum of a plurality of said output signals from a plurality of said target areas of said medium; and
   a combination thereof.

17. The system of claim 15 wherein said threshold amplitude is a product of said reference amplitude and a predetermined factor.

18. The system of claim 13 wherein said similar amplitudes of said plurality of said points are one of those greater than said threshold amplitude and those less than said threshold amplitude.

19. The system of claim 1 wherein said signal analyzer includes:
   a threshold unit for providing a threshold range of said amplitudes;
   a comparison unit for comparing said amplitudes of said first output signal with said threshold range; and
   a selection unit for identifying said plurality of said points of said first output signal.

20. The system of claim 19 wherein said similar amplitudes of said plurality of said points are one of those falling within said threshold range and those falling outside said threshold range.

21. The system of claim 1 wherein said signal processor includes an averaging unit for calculating said first baseline as an average of said similar amplitudes, wherein said average is one of:
   an arithmetic average of said similar amplitudes;
   a geometric average of said similar amplitudes;
   a weight-average of said similar amplitudes; and
   an ensemble-average of said similar amplitudes.

22. The system of claim 1 wherein said signal processor includes a calibration unit for providing said self-calibrated first output signal by normalizing said first output signal by said first baseline thereof.

23. The system of claim 22 wherein said self-calibrated first output signal is one of:
   a ratio of said first output signal to its first baseline; and
   a ratio of a difference between said first output signal and its first baseline to said first baseline.

24. The system of claim 1 wherein said signal analyzer includes at least one filter unit configured to improve signal-to-noise ratio of said first output signal.

25. The system of claim 24 wherein said filter unit includes at least one of:
   an averaging unit configured to provide at least one of an arithmetic average, geometric average, ensemble-average, and weight-average of a plurality of said first output signals from said first target area; and
   a low pass filter configured to remove high frequency noise from said first output signal.

26. The system of claim 1 wherein said signal analyzer further includes a control unit configured to store a plurality of said baselines measured in a plurality of target areas of said medium and to compare at least one of said baselines with the others thereof.

27. The system of claim 26 wherein said control unit is configured to provide an average of said plurality of said baselines.

28. The system of claim 26 wherein said control unit is configured to generate a signal when at least one of said baselines is at least substantially different from at least one of the others thereof.

29. An optical imaging system configured to generate images of target areas of a physiological medium, said images representing distribution of chromophores or properties thereof in said target areas, said system including at least one wave source configured to irradiate electromagnetic waves into said medium and at least one wave detector configured to detect electromagnetic waves from said medium and to generate output signal in response thereto, said system comprising:
   a signal analyzer configured to receive a first output signal from said wave detector, to analyze amplitudes of said first output signal, and to select a plurality of points of said first output signal having substantially similar amplitudes, wherein said first output signal is representative of said distribution in a first target area of said medium;
   a signal processor configured to calculate a first baseline predominantly from said first output signal and to provide a self-calibrated first output signal by manipulating both of said first output signal and its first baseline, where said first baseline corresponds to a representative amplitude of said similar amplitudes; and
   an image processor configured to construct said images of said distribution of at least one of said chromophores and said properties thereof from said self-calibrated first output signal.

30. A method for obtaining a calibrated output signal from an optical imaging system having an optical probe with at least one wave source configured to irradiate near-infrared electromagnetic waves into target areas of a physiological medium and at least one wave detector configured to generate output signal in response to said near-infrared electromagnetic waves detected thereby, the method comprising:
   positioning said optical probe on a first target area of said medium;
   generating a first output signal without displacing said optical probe from said first target area;
   identifying at least one first portion of said first output signal, wherein the signal in said first portion has substantially similar first amplitudes; and
   obtaining a first baseline of said first output signal as a representative value of said substantially similar first amplitudes.

31. The method of claim 30 further comprising:
   normalizing said first output signal by said first baseline to provide a self-calibrated first output signal.

32. The method of claim 31 wherein said normalizing step comprises:
providing a ratio signal representing a ratio of said first output signal to its first baseline.

33. The method of claim 31 wherein said normalizing step comprises:
providing a difference signal representing a difference between said first output signal and its first baseline; and
providing a ratio signal representing a ratio of said difference signal to said first baseline of said first output signal.

34. The method of claim 30 wherein said generating step comprises:
providing movement of at least one of said wave source and detector over said first target area; and
generating said first output signal during said movement.

35. The method of claim 30 further comprising:
reducing noise from said first output signal prior to performing at least one of said identifying and obtaining steps.

36. The method of claim 35 wherein said reducing step comprises at least one of:
arithmetically averaging a plurality said first output signals;
geometrically averaging a plurality of said first output signals;
weight-averaging a plurality of said first output signals;
ensemble-averaging a plurality of said first output signals; and
processing at least a portion of said first output signal through a low-pass filter.

37. The method of claim 30 wherein said identifying step comprises one of:
selecting a threshold amplitude and identifying said first portion having said amplitudes greater than said threshold amplitude;
selecting a threshold amplitude and identifying said first portion having said amplitudes less than said threshold amplitude;
selecting at least one threshold range and identifying said first portion having said amplitudes falling within said threshold range; and
selecting at least one threshold range and identifying said first portion having said amplitudes falling outside said threshold range.

38. The method of claim 37 wherein said selecting step comprises one of:
manually selecting at least one of said threshold amplitude and range; and
providing a reference amplitude and providing at least one of said threshold amplitude and range based on said reference amplitude.

39. The method of claim 38 wherein said reference amplitude is one of:
a local maximum of said first output signal from said first target area;
a local minimum of said first output signal from said first target area;
an average of at least one portion of said first output signal;
a global maximum of a plurality of said output signals from a plurality of said target areas of said medium;
a global minimum of a plurality of said output signals from a plurality of said target areas of said medium; and
and a combination thereof.

40. The method of claim 38 wherein said providing step comprises:
multiplying said reference amplitude by a pre-selected factor to provide at least one of said threshold amplitude and range.

41. The method of claim 30 wherein said obtaining step comprises one of:
arithmetically averaging said similar amplitudes;
geometrically averaging said similar amplitudes; and
weight-averaging said similar amplitudes.

42. The method of claim 30 further comprising:
displacing said optical probe to a second target area of said medium;
generating a second output signal from said second target area; and
normalizing said second output signal by said first baseline of said first target area to provide a self-calibrated second output signal.

43. The method of claim 42 further comprising:
repeating said displacing and generating steps of claim 43 in a plurality of said target areas of said medium.

44. The method of claim 30 further comprising:
displacing said optical probe to a second target area of said medium;
generating a second output signal from said second target area;
identifying at least one second portion of said second output signal, wherein said second portion has substantially similar second amplitudes; and
obtaining a second baseline of said second output signal as a representative value of said substantially similar second amplitudes.

45. The method of claim 44 further comprising:
calculating a composite baseline by averaging said first baseline from said first target area and said second baseline from said second target area; and
normalizing said first and second output signals by said composite baseline.

46. The method of claim 45 wherein said calculating step comprises one of:
arithmetically averaging said baselines;
weight-averaging said baselines; and
selecting one of said baselines as said composite baseline.

47. A method for obtaining a calibrated output signal from an optical imaging system including an optical probe with at least one wave source and at least one wave detector, said wave source configured to irradiate near-infrared electromagnetic waves into target areas of a physiological medium which includes a normal region and an abnormal region, said wave detector configured to generate output signal in response to said near-infrared electromagnetic waves detected thereby, said method comprising:
positioning said optical probe on a first target area of said medium;
generating a first output signal without displacing said optical probe from said first target area;
identifying at least one first portion of said first output signal attributed to said normal region of said target area; and
obtaining a first baseline of said first output signal from a representative value of said first portion of said first output signal, wherein said first portion attributed to said normal region is characterized by substantially flat profile and by substantially similar first amplitudes.

48. A method for calibrating an optical imaging system having an optical probe with at least one wave source for irradiating near-infrared electromagnetic waves into target areas of a physiological medium and at least one wave detector for generating output signals in response to near-infrared electromagnetic waves detected thereby, said method comprising:

positioning said optical probe on a first target area of said medium;

generating a first output signal without displacing said optical probe from said first target area;

identifying at least one first portion of said first output signal having substantially similar first amplitudes before displacing said optical probe from said first target area; and obtaining a first baseline of said first output signal from a representative value of said substantially similar amplitudes before displacing said optical probe from said first target area.

49. The method of claim 48 further comprising:

normalizing said first output signal by said first baseline to provide a self-calibrated first output signal on a substantially real time basis.

50. The method of claim 49 further comprising:

generating at least one of images of said first output signal, images of said self-calibrated first output signal, images based on said first output signal, and images based on said self-calibrated first output signal.

* * * * *